(12) United States Patent
Gutman (10) Patent No.: US 6,580,940 B2
(45) Date of Patent: Jun. 17, 2003

(54) X-RAY SYSTEM WITH IMPLANTABLE NEEDLE FOR TREATMENT OF CANCER

(76) Inventor: George Gutman, 1109 Yorkshire Rd., Birmingham, MI (US) 48009

( * ) Notice: Subject to any disclaimer, the term of this patent is extended or adjusted under 35 U.S.C. 154(b) by 88 days.

(21) Appl. No.: 09/776,559

(22) Filed: Feb. 2, 2001

(65) Prior Publication Data

US 2002/0003856 A1 Jan. 10, 2002

Related U.S. Application Data

(60) Provisional application No. 60/179,842, filed on Feb. 2, 2000, and provisional application No. 60/196,060, filed on Apr. 10, 2000.

(51) Int. Cl.[7] ................................................. A61N 5/10
(52) U.S. Cl. ............................ 600/427; 378/65; 378/64
(58) Field of Search ........................... 378/65, 152, 84; 600/427; 606/15, 7; 604/890.1

(56) References Cited

U.S. PATENT DOCUMENTS

| | | | |
|---|---|---|---|
| 4,913,142 A | * 4/1990 | Kittrell et al. | ................. 378/84 |
| 5,153,900 A | 10/1992 | Nomikos | ...................... 378/65 |
| 5,369,679 A | 11/1994 | Sliski | ............................ 378/65 |
| 5,422,926 A | 6/1995 | Smith | ........................... 378/121 |
| 5,428,658 A | 6/1995 | Oetittinger | ................... 378/119 |
| 5,528,652 A | 6/1996 | Smith | ........................... 378/65 |
| 5,566,221 A | 10/1996 | Smith | .......................... 378/145 |
| 5,646,976 A | 7/1997 | Gutman | ....................... 378/84 |
| 5,799,056 A | 8/1998 | Gutman | ....................... 378/84 |
| 6,014,423 A | * 1/2000 | Gutman et al. | ................ 606/15 |
| 6,389,100 B1 | * 5/2002 | Verman et al. | ................ 378/84 |

* cited by examiner

Primary Examiner—Marvin M. Lateef
Assistant Examiner—Barry Pass
(74) Attorney, Agent, or Firm—Brooks & Kushman P.C.

(57) ABSTRACT

An x-ray system for treatment cancer by delivering x-ray radiation directly to a desired region of tissue comprising an x-ray source with directed narrow space distribution of x-rays (linear accelerator), conditioning optics which direct and monochromotize x-ray radiation, an implantable needle with means for shaping beam installed across the x-ray beam, and expanding pipe-guide connecting conditioning optics with implantable needle whereby the energy, intensity, and space distribution of the delivered to the tumor x-ray radiation may be adjusted in accordance with the predefined treatment requirements.

15 Claims, 13 Drawing Sheets

X-RAY SYSTEM WITH IMPLANTABLE NEEDLE FOR TREATMENT OF CANCER

CROSS-REFERENCE TO RELATED APPLICATIONS

This Application claims the benefit of priority under 35 U.S.C. §119(e) of U.S. Provisional Application Ser. No. 60/179,842 filed on Feb. 2, 2000, and U.S. Provisional Application No. 60/196,060 filed on Apr. 10, 2000, both of which are incorporated herein by reference.

BACKGROUND OF THE INVENTION

1. Field of the Invention

The present invention relates to the use of an x-ray system for cancer treatment. More specifically, the present invention relates to the use of an x-ray system with an implantable needle for treating tumors.

2. Background Art

There currently exist x-ray systems which include lower power x-ray devices (x-ray tubes) which are implantable into a patient's body for directly irradiating a desired region of tissue with the x-ray. The ability to deliver x-ray radiation to the tumor is the main advantage this system. For tumor treatment, Compton scattering and photoionization are the most important effects of interactions of x-ray radiation with biological samples. For the dominant photoelectric effect the probability of atom ionization decreases with increasing photon energy as an inverse third-power law. In other words, an x-ray beam with the energy of 10 keV delivered directly to the tumor will be 125 times more effective when absorbed compared with a 50 keV x-ray beam. But low energy radiation provides very limited penetration of tissue, and is thus useful only in treating skin lesions.

The known x-ray device miniaturized low power x-ray source U.S. Pat. No. 5,153,900, Oct. 6, 1992) which is implantable into a patient body for direct delivery of x-ray radiation has the following disadvantages:

1. The tube has very limited power, because the x-ray source should be small enough to be implanted into the body. For treatment of tumors, for example brain tumors, a high dose rate for single dose irradiation is generally preferred, therefore this tube does not provide sufficient radiation as required for treatment.
2. High vacuum x-ray sources with high voltage (up to 90 kV) are difficult to implant into a human body.
3. Besides including predefined "useful" x-ray energy, the spectrum of the x-ray beam also includes an x-ray energy continuum, known as bremsstrahlung, which can destroy healthy tissue.
4. During relatively long exposures (several minutes) the temperature of anode which is set on the end of implantable x-ray source may rise sufficiently.
5. The x-ray device should be used in environments in which there are low level dc and ac magnetic fields which are capable of deflecting the electron beam from the anode of implantable x-ray source. Special measures therefore need to be taken against the influence of outside electric fields on an electron beam.
6. There is a large (from 5 to 7 mm) diameter for the implantable x-ray source.

It would therefore be useful to develop an x-ray device which can overcome the obstacles set forth above.

SUMMARY OF THE INVENTION

According to the present invention, there is provided a method and apparatus for the treatment of cancer by delivering x-ray radiation directly to a desired region of tissue, including tumors. An object of the present invention is to allow adjustment in energy, flux intensity, and shape of the x-rays delivered to the tissue, utilizing an x-ray tube or a linear accelerator with a thin anode, any known type of conditioning optics (multilayer optics, crystal, capillar optics, aperture, and etc.) which direct x-ray radiation and implantable needles with the means for shaping x-ray radiation. Another object of the present invention is to increase x-ray flux directed to the needle through the use of a linear accelerator with a thin anode. This modified accelerator has a narrow sharp space distribution of emitted x-ray radiation even for a low energy (50 kV and less) x-ray beam. For optics with a small (less than 1 degree) angular aperture, this x-ray source allows a more than three orders of magnitude increase in flux directed to the needle.

DESCRIPTION OF THE DRAWINGS

Other advantages of the present invention will be readily appreciated as the same becomes better understood by reference to the following detailed description when considered in connection with the accompanying drawings wherein:

FIGS. 13 A and B are diagrams showing the delivery of 100% of the proper dose to a tumor using $^{192}$Ir and an x-ray beam.

DETAILED DESCRIPTION OF THE INVENTION

Generally, the present invention provides an x-ray system, which uses x-rays to treat tumors by delivering the x-rays directly to the tumor through a needle 17 that is implanted in the tumor. The approach is similar to high dose rate (HDR) Brachytherapy with the advantage of being able to deliver radiation with a pre-calculated energy, intensity and special distribution to different parts of the tumor. This ability guarantees significantly better control of critical organ dose. The radiation dose can be diminished in accordance with the predefined treatment requirements to spare surrounding normal tissue and structures from excessive radiation. Additionally, the system requires fewer needle insertions than HDR Brachytherapy to deliver the same levels of radiation dosage.

The x-ray system 10 of the present invention uses as an x-ray source with directed narrow space distribution of radiation (a linear accelerator 44) coupled with collimating optics 13 (Gutman optics in particular). The metal anode of the linear accelerator has a thickness of less than 50 $\mu$m. In accordance with a computer simulation, there is created a narrow space distribution, even for low energy (10 k V–50 k V) x-rays. Further, the system can function by placing an anode 42 of the accelerator tube 46 at a small (less than 10°) angle relative to the optical axis 16 of the accelerated electron beam 41. (FIG. 1C).

The system also includes an expanding pipe guide and an implantable hollow needle. The collimating optics form a monochromatic parallel x-ray beam with a diameter less than 400 microns, which is further directed through the connector-guide. The parallel x-ray beam which has passed through the connector-guide is then directed through a hollow needle that has an inserted changeable pseudo-target. When the parallel x-ray beam irradiates the pseudo-target, it emits x-ray radiation with an energy defined by the characteristic line of the target material (from 20 keV to 100 keV). The x-rays irradiate a tumor through the needle walls. The pseudo-target serves as a fully controllable x-ray source located at the center of the tumor. Thus, the x-ray system allows delivery of 100% of the dose inside the tumor without harming the surrounding tissue.

The x-ray system 10 of the present invention includes an implantable needle 17 with a defined cut off angle reflecting crystal 20 which is installed across the axis of the beam and a back window 21 of the implantable needle 17, for transmission of the radiation.

In the preferred embodiment of the present invention the reflecting crystal 20 is in the shape of pyramid whereby every side of the pyramid is made up of reflecting crystals 20 with pre-calculated cut off angles. Alternatively, the reflecting crystal 20 can be in the shape of a cone wherein the back surface of the cone is a reflecting crystal 20 with a pre-calculated cut off angle.

In another embodiment of the present invention, the implantable needle 17 contains a metal quasi-anode installed across the beam and a back window 21, for transmission of the radiation. The quasi-anode can be in the shape of a pyramid or cone. The quasi-anode can be built from sections, such that every section uses a different material (metal) to emit radiation with a different energy.

Alternatively, the implantable needle 17 can contain a metal coated end window which, when being irradiated with the parallel or focusing x-ray incident beam, produces fluorescent x-rays acting as a linear or point x-ray focus source.

In another embodiment of the present invention, the implantable needle 17 is made of walls which are transparent in the x-ray emitted by quasi-anode.

The x-ray system 10 of the present invention can also include conditioning (focusing or collimating) optics 13 and an expanding pipe guide 14. The expanding pipe guide 14 ensures independent relative x-ray source movement of the needle 17 along the optical axis 16 (x-ray beam 40). The guide can also contain rotating parts which ensure rotation of the needle 17 around the x-ray beam 40 in an optical axis 16.

Figure 1A:
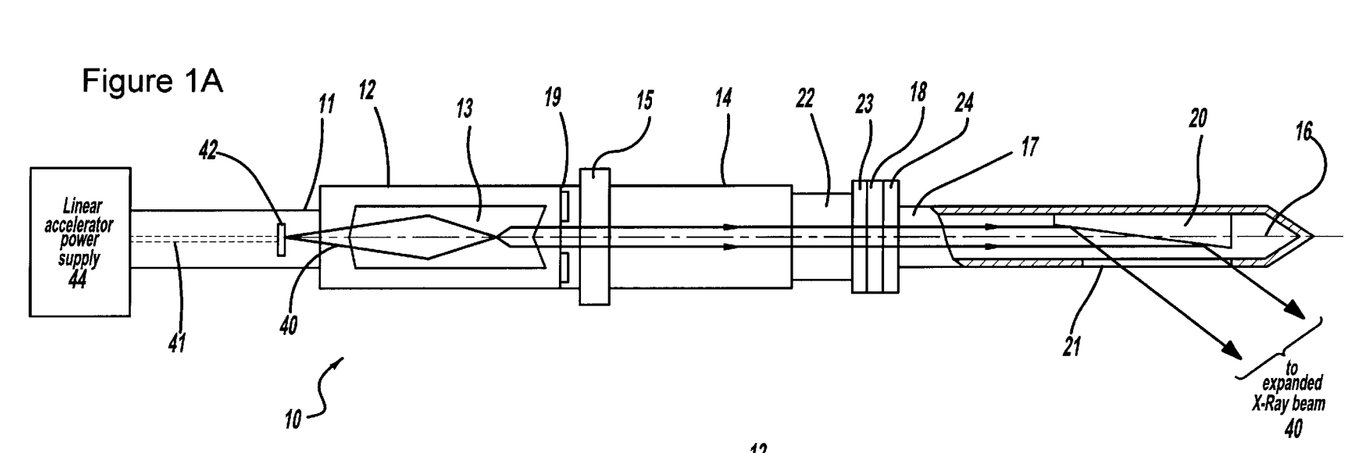
FIGS. 1A–C are schematic views of the first embodiment of the present invention, including a linear accelerator as an x-ray point source, collimating optics, an expanding pipe guide, and an implantable needle.
Figure 1B:
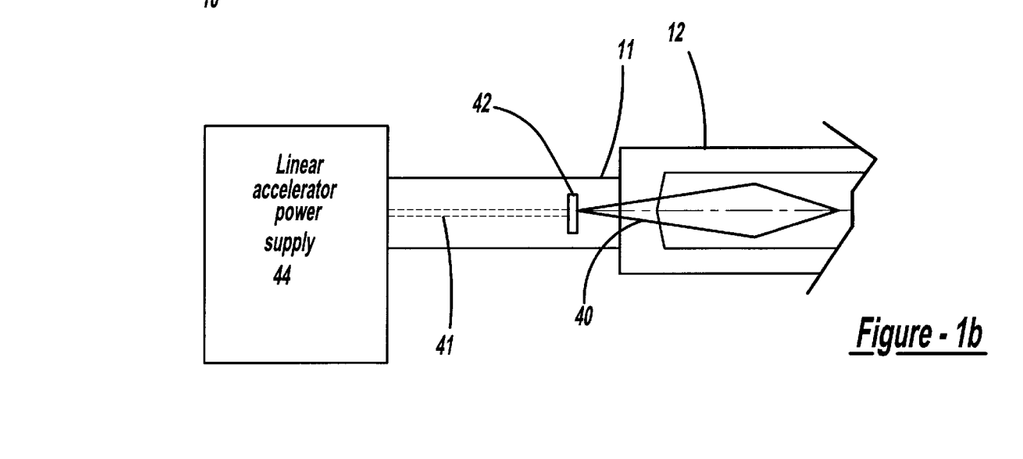
Figure 1C:
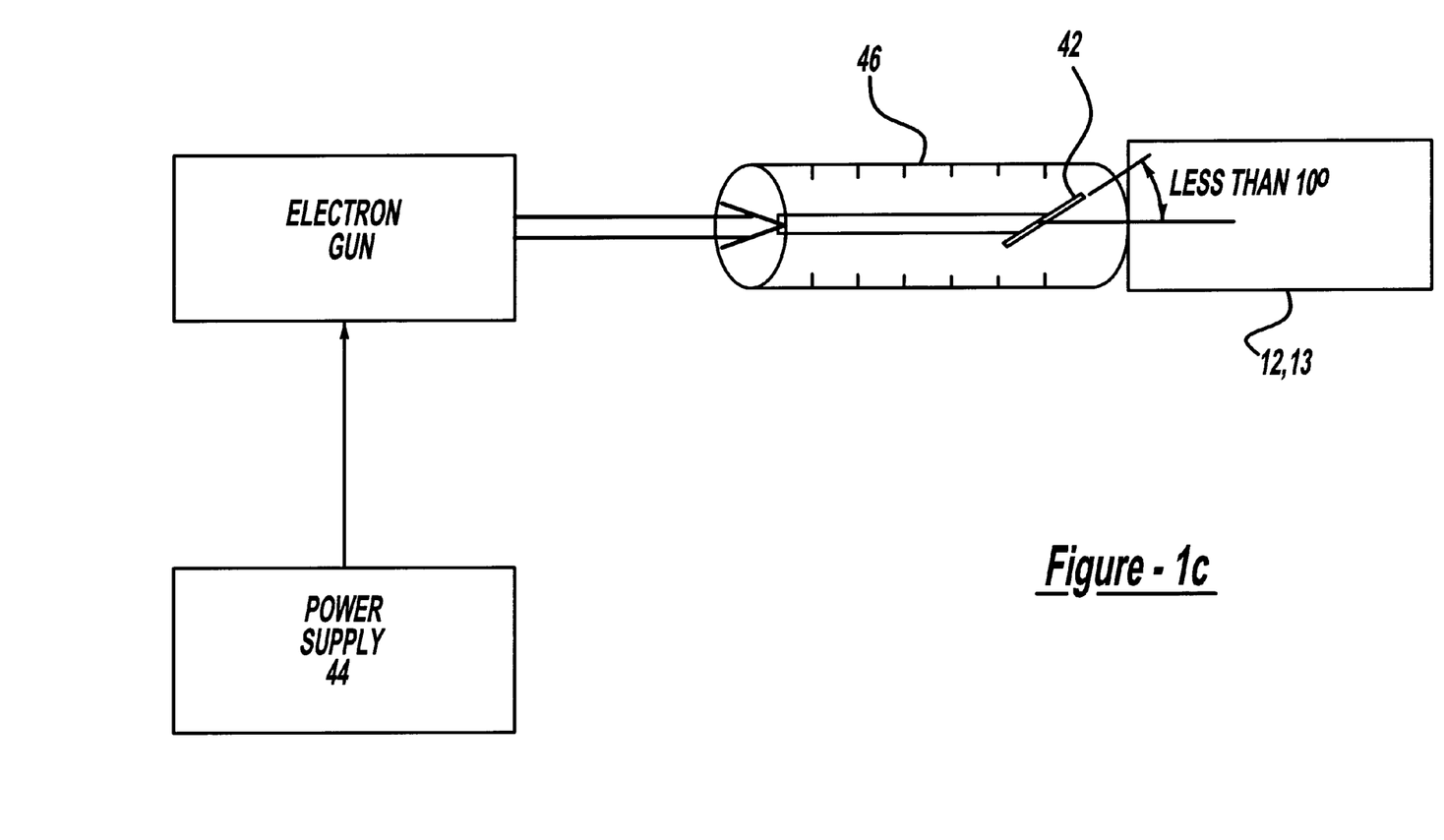

More specifically, FIG. 1 shows an x-ray system 10 embodying the present invention. The x-ray system 10 includes linear accelerator (linac) 11 with a power supply 44 and a control panel. The thickness of an anode depends on used energy of x-rays, but does not exceed 50 $\mu$k. To protect the anode of linac against overheating and maintaining a small point focus size the anode is set under small (less than 10 degrees) incident angle relatively accelerating electrons. (FIG. 1A). In other words, the physical dimensions of the focus are for example, 0.3×3 mm whereas for conditioning optics the point focus is 0.3×0.3 mm (for 6 degree incident angle).

Also included in the system is a housing 12 with collimating (or focusing) optics 13 and variable slits 19. An elongated pipe guide 14 of variable length, extends from the reference plate 15 of the housing 12 along an optical axis 16 to a needle reference plate 24. An implanted needle 17 also extends along an optical axis 16 from a rotating plate 18 of the elongated pipe guide 14. The plate 18 can rotate relative to the reference plate 23 using a laterally moving shift 22. Crystal 20 which has a pre-calculated cut off angle and d-spacing which crosses the x-ray beam 40 and guarantees the expanding x-ray beam 40 in a longitudinal direction. The needle 17 also has a back window 21 for the exit of radiation. The window 21 can be made of Beryllium (Be), Carbon (C) or other low absorption materials, including biocompatible plastic. The outer surface of the beryllium window 21 can be coated with a biocompatible plastic.

In another embodiment of the present invention, the needle 17 is a hollow tube 22 (FIG. 6) with an outer diameter of 2 mm and inner diameter of 0.8 mm which is symmetrical relative to the optical axes. The connector, which can telescope and rotate, insures proper implantation of the needle 17 when placed in soft tissue. This ensures proper alignment of the needle 17 along the optical axis 16 without any bending of the needle. A metallic quasi-anode can move along the needle 17 by a special mechanism of the connector in accordance with pre-calculated law.

A needle 17 can be made from a magnesium-boron alloy, titanium or other similar materials. The walls of the needle 17 are practically "transparent" for the fluorescent and scattering x-ray radiation. Using different materials for needles 17 and quasi-targets 42 we can change both the shape and "fall off" curve of the delivered x-ray beam 40.

The x-ray beam 40 from the point focus x-ray source is directed to the collimating optics 13. The collimating optics 13 can create a monochromatic parallel x-ray beam 40 in two dimensions from a point source.

Figure 6:
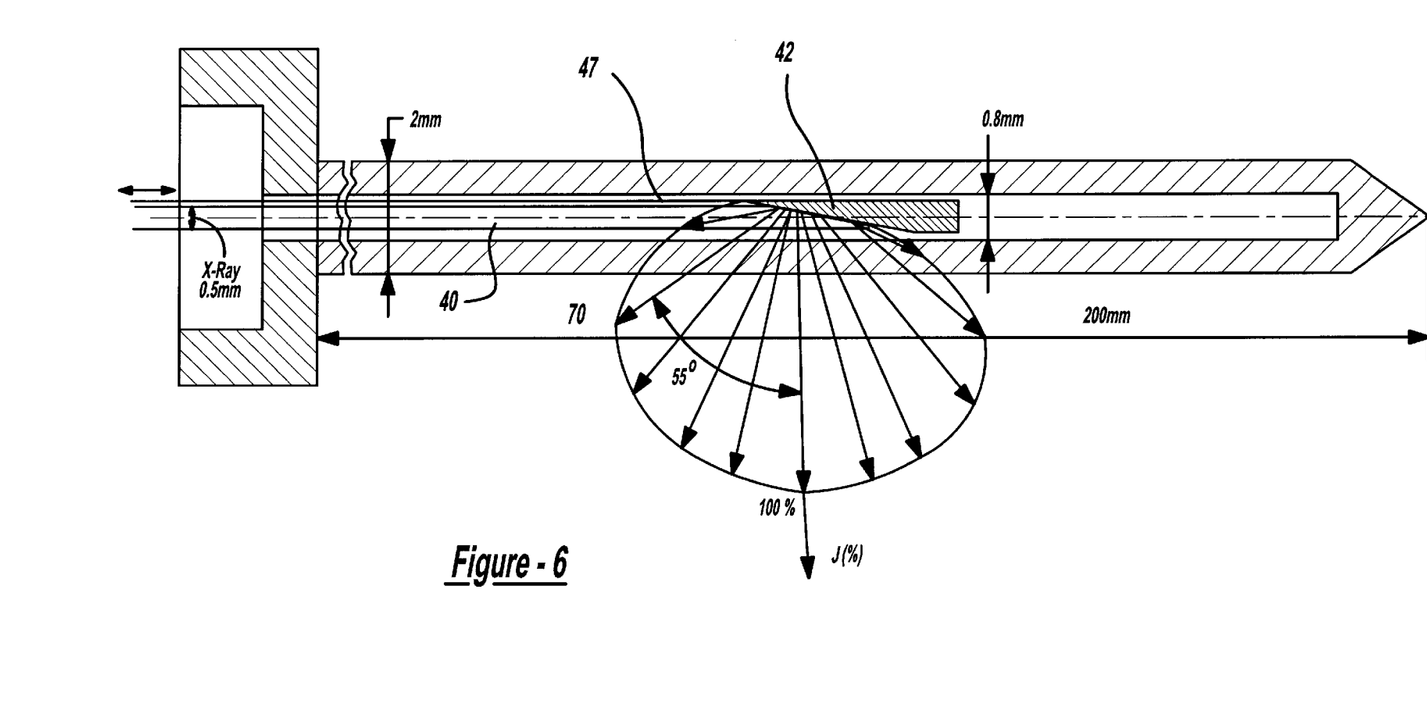
FIG. 6 is a cross-sectional view of the needle with a quasi-anode and transparent needle walls.

The x-ray beam 40 is then directed through a hollow needle 17 which has a special target 42. When the x-ray beam irradiates the pseudo-target, it emits x-ray radiation. This radiation has a space distribution close to semispherical in shape and penetrates through the walls or side window(s) and irradiates the tumor (FIG. 6). This system allows accurate positioning of the source of predetermined x-ray radiation to the desired region, in particular, inside of the tumor.

It is possible to change the x-ray dose by changing, the angular velocity of the target 42 inside the needle 17 (FIG. 6), changing intensity of x-ray source or both. The rotation of the needle 17, changing x-ray beam 40 intensity, and changing of the beam shape during the process of treatment can be under the control of a computer system.

Figure 2:
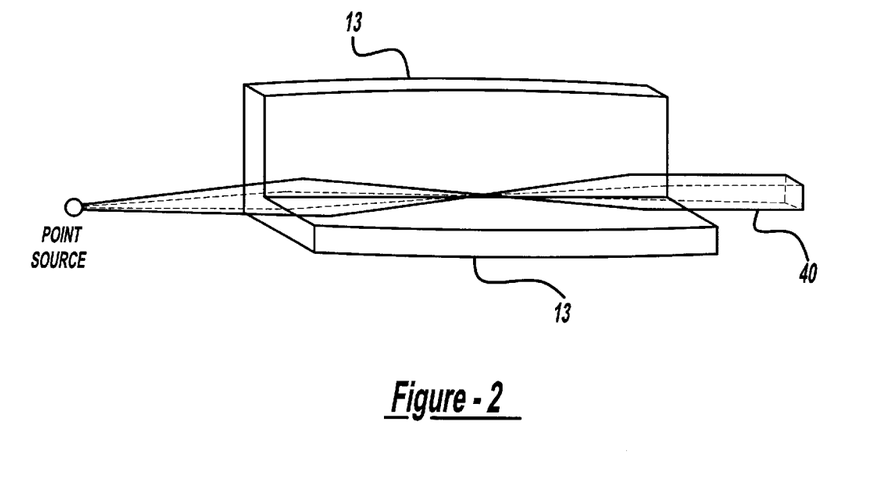
FIG. 2 is a cross-sectional schematic view of the collimating optics including a pair of parabolic x-ray monochromators with laterally graded d-spacing multilayer coatings, providing a monochromatic, highly parallel x-ray beam.
Figure 4:
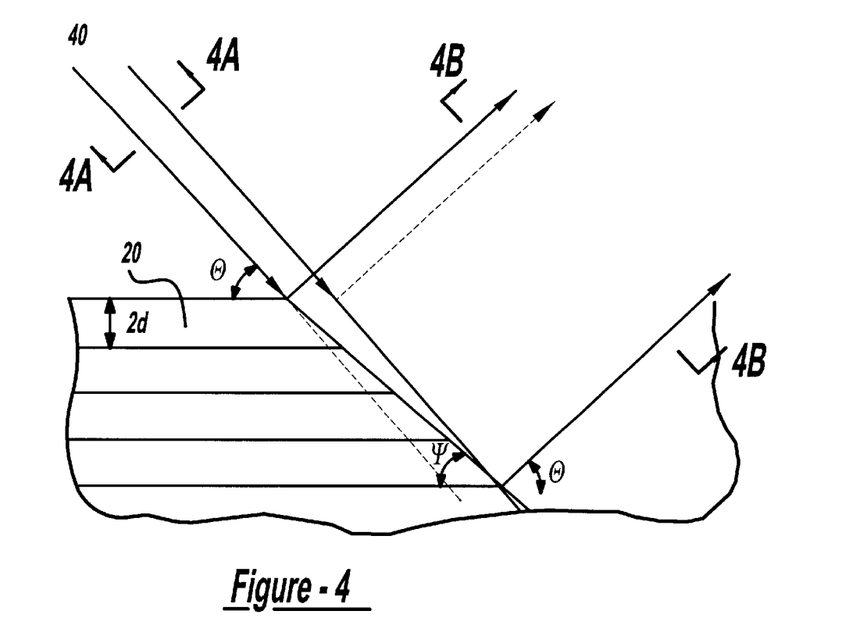
FIG. 4 shows increasing the size of incident beam 40 (in one dimension) after reflection from the crystal within take off angle $\Psi$. Here, $\theta$-Bragg angle (angle of reflection) $\Psi$-take off angle (angle between surface of a crystal and lattice of a crystal), further showing a cross-section of the incident beam shown on FIG. 4A and a cross-section of the reflected beam shown on FIG. 4B.
Figures 4A, 4B:
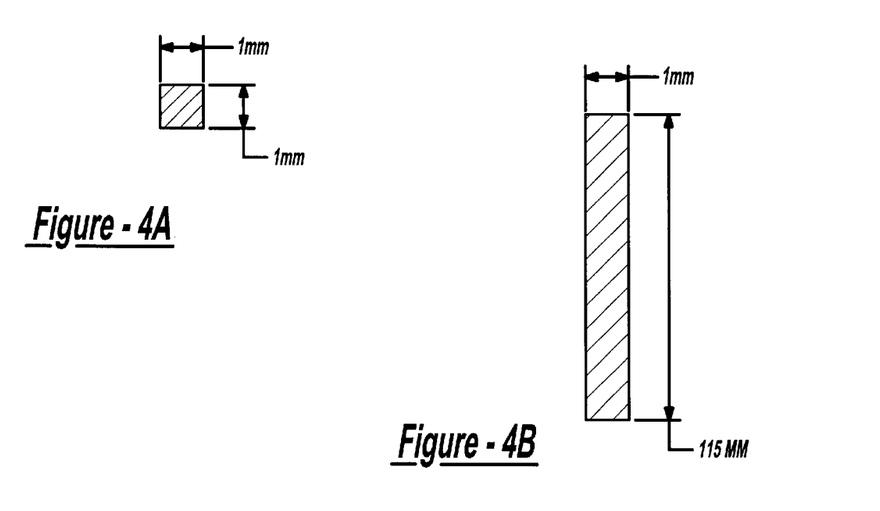
FIGS. 4A and 4B are schematic views of a parallel x-ray beam reflected from the crystal which is designed and fabricated with a pre-calculated cut off angle.
Figure 4C:
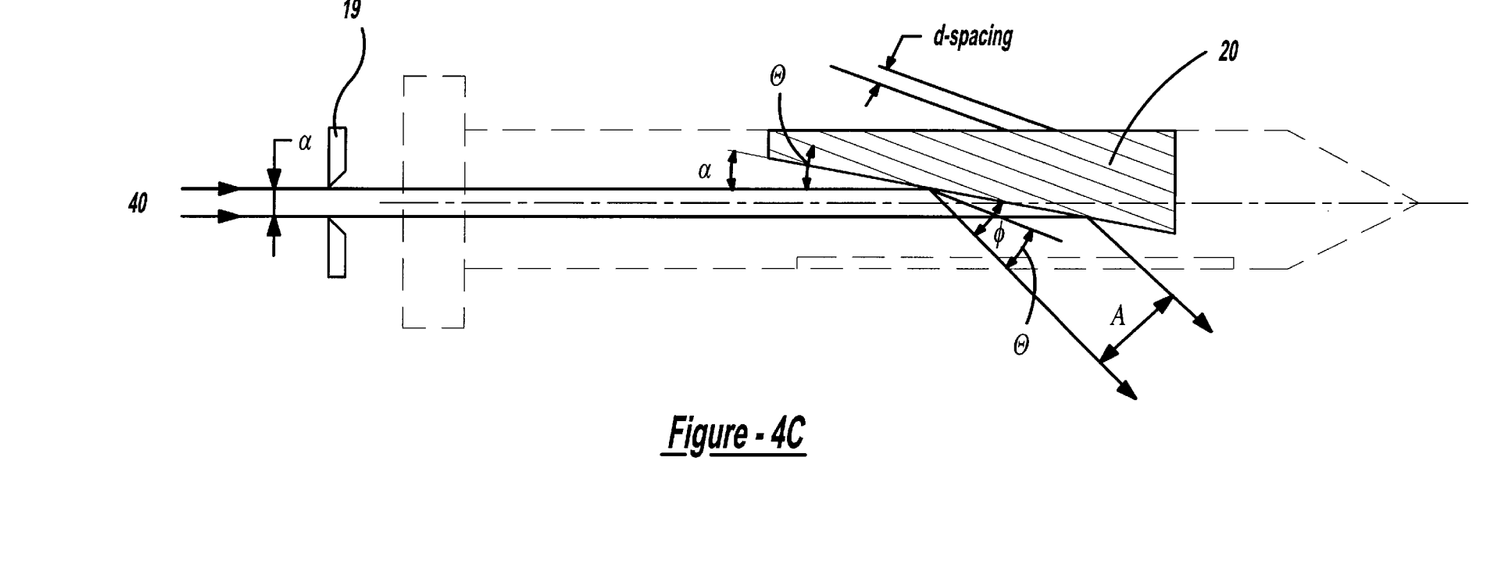
FIG. 4C shows the crystal with take-off angle $\alpha$ and Bragg angle $\theta$ installed in the needle to "create" a fan shape for reflected beam.

The housing 12 with the collimating optics 13 (the optical schematic is shown on FIG. 2) is mounted on the x-ray source in such a way as to guarantee proper positioning of the point focus of the x-ray source which is in focus in the optical schematic. A "side by side" Kirkpatrick-Baez (K-B) optical configuration (FIG. 2) employing two Gutman Optics of parabolic shape 50 generates a high precision parallel monochromatic x-ray beam 40 extending along an optical axis 16. Variable slits 19 ensure proper shaping of the x-ray beam 40 in the longitudinal direction (FIG. 4C) even during treatment.

Generally, the conditioning (collimating/focusing) multi-layer optics are used for x-ray beams 40 with energy up to 60 keV. For higher, up to 120 keV, x-ray beam 40 energy other methods of x-ray beam conditioning are used. These methods can be as simple as using an aperture to limit the x-ray beam 40, using monochromators (graphite monochromator, in particular) or using total reflection for a grazing incident x-ray beam 40. In the last-named case, metallic or metal (Au, Pt, etc.) coated mirrors work in the K-B scheme, providing a polychromatic conditioning beam.

The expanding pipe guides (FIG. 3) are used for movement of the implantable needle 17 along the x-ray beam 40 and for rotation of the needle 17 around the x-ray beam 40 on an optical axis 16.

Figure 3:
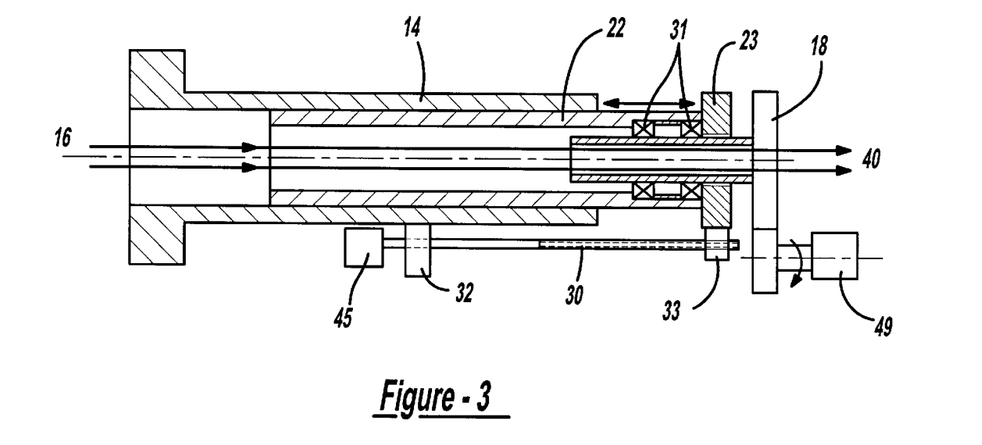
FIG. 3 is a schematic view of the extending or expanding pipe guide ensuring both movement of the implantable needle along the x-ray beam and rotation of the needle around the x-ray beam.

A hollow tube 22 can move inside of a stationary tube 14 along of an optical axis 16. A screw holder 32 is mounted on the fixed tube 14 and a nut holder 33 is mounted on the moving tube 22. A stepper motor 45 rotates a screw 30 thus ensuring that linear movement 22 occurs relative to the fixed tube 14. Two bearings 31 are installed inside the linear moving tube 22 ensuring that the rotation reference plate 18 maintains its place relative to the flange 23 of the moving tube 22. The stepper motor 45 is used for rotation with a reference plate 18. The described system guarantees smooth and precise computer control linear movement and rotation of the needle 17 mounted on the reference plate 18.

In a preferred embodiment, the implantable needle 17 (FIG. 1) is a hollow stainless cylinder from 10 to 20 cm in length with interior diameter of 2 mm and an exterior diameter of 1.2 mm. The reference plate 24 guarantees the precise mounting of the needle 17 on the extender guide, as shown in FIG. 1. The needle 17 contains a back beryllium (Be) window 21 for transmission of the x-ray beam 40. The outside surface of the window 21 can be coated with a biocompatible plastic. The window 21 also can be made of any low absorption materials as carbon (C), etc. To expand the x-ray beam 40 and direct the x-ray beam 40 into the window 21 the reflecting crystal 20 is mounted inside of the needle 17.

With regard to the reflection and expansion of the reflecting x-ray beam 40, it is known that x-ray radiation reflects from the crystal 20 in accordance with Bragg Law:

$$n\lambda = 2d \sin\Theta$$

Where $\lambda$—wavelength of incident beam $2d$—the lattice spacing of a crystal $\Theta$—angle of incidence $n$—the order of the reflection The structure of crystalline solid, a regular three dimensional array of atoms, forms a natural diffraction grating for x-rays. The quantity $2d$ (FIG. 4) in the Bragg equation is the perpendicular distance between the planes of atoms in the crystal 20.

If x-rays reflect from the flat crystal 20, the cross-section of the reflecting beam does not change. Cross-section "a—a" is the same as cross-section "b—b" (FIG. 4A), but if the crystal 20 is cut as shown (FIG. 4; $\psi$—cut off angle), the cross-section "a—a" increases in one dimension in accordance with equation:

$$A = a/\sin_\alpha$$

Where $\alpha$ (FIG. 4C) is the angle between the incident beam and the cut off angle of the crystal 20.

For example, if the wavelength of conventional x-ray source with Cu anode: $\lambda = 1{,}542$ Å, and as the reflecting crystal 20 use LiF220 with $2d = 2.848$ Å. Using the Bragg equation, $\Theta = 32.8°$.

The crystal 20 is cut at angle $\psi = 32.3°$. The crystal 20 is installed in the center of the needle 17 at the angle of $\alpha = 0.5°$ between incident beam and surface of the crystal 20. Keeping the angle of incidence, $\Theta = 32.8°$, if a cross-section of the incident beam was 1×1 mm (usual cross-section of the beam for Cu radiation), the cross-section of reflecting beam increases up to 1×115 mm (1 mm/sin 0.5°), and the angle of reflection relative to the optical axis 16 of the needle 17 is $\psi = 2\Theta - \alpha$ and $\psi = 65.1°$.

Figure 5A:
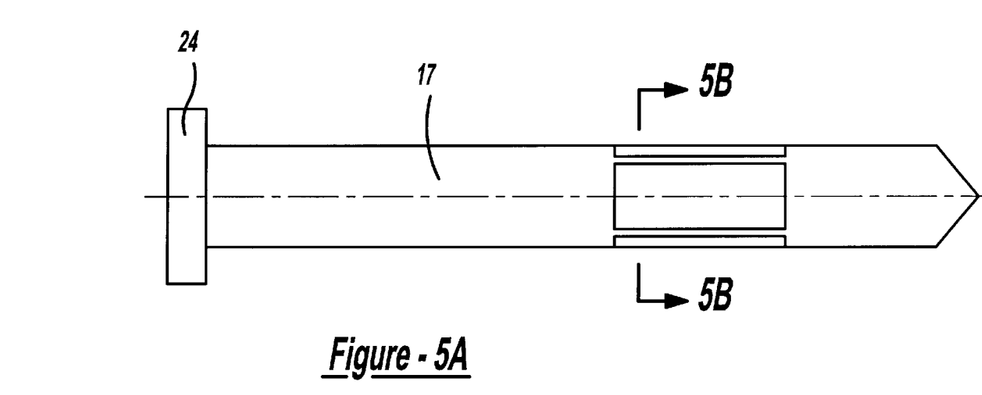
FIG. 5 is a schematic view and cross-section of the needle with back windows which are used for transmitting x-ray beams reflecting from a pyramidal crystal.
Figure 5B:
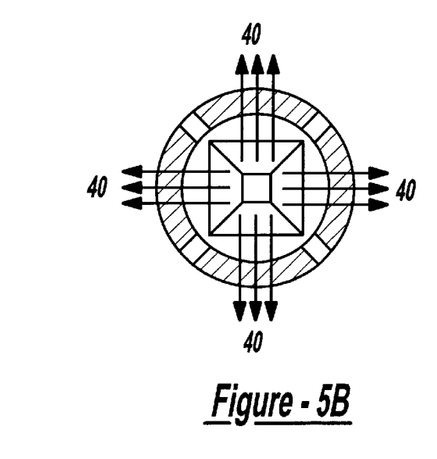
Figure 5C:
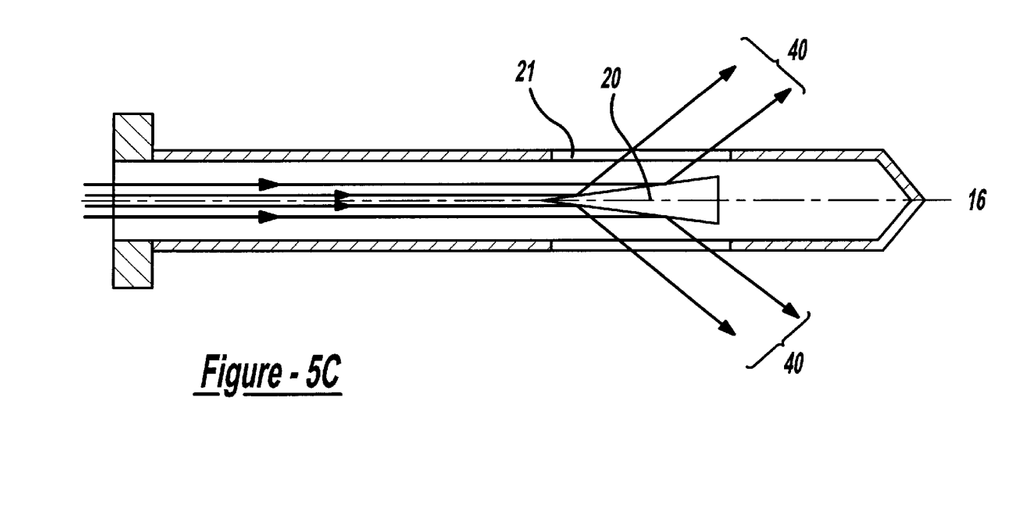

It is possible to use instead of a flat crystal 20 a crystal 20 with a pyramid shape (FIG. 5). Every back side of the pyramid is a crystal 20 with the same cut off angle as a flat crystal 20. The pyramid is installed symmetrically, relative to the optical axis 16. In this case the needle 17 has four windows. The crystal 20 can even have a cone shape (designed and mounted identically to pyramid). A cylindrical beryllium window 21 can be used for transmission of x-ray radiation in all directions.

For special applications it is possible to use a narrow parallel x-ray beam 40. In this specific case the reflecting crystal 20 is not used and the needle 17 has an end window for direct transmission of radiation. If it is necessary to get ultra small focus of the x-ray beam 40, focusing optics 13 (with elliptical mirrors instead of parabolic ones) can be applied. Focus of up to 10 micron can be achieved.

It is known that the x-ray beam 40 can interact with material, metal in particular, thereby producing characteristic x-rays (fluorescent radiation) analogous to the characteristic x-rays which are emitted from the anode of the x-ray source. The main difference is the amount of "noise" for fluorescent radiation, this is significantly lower in comparison with the spectrum of an x-ray source where bremsstrahlang x-rays are added to the characteristic spectrum. The energy of the fluorescent radiation is defined by the irradiating material (z-number) and the parameters of the incident x-ray beam 40.

Figure 7A:
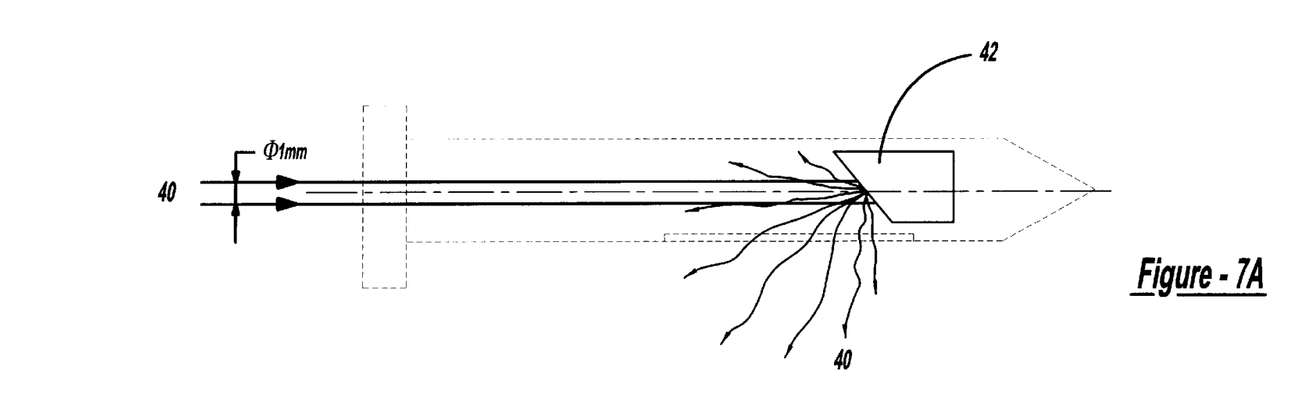
FIGS. 7A and 7B are a schematic views of the emitting of fluorescent radiation by a metal quasi-anode installed in the needle.
Figure 7B:
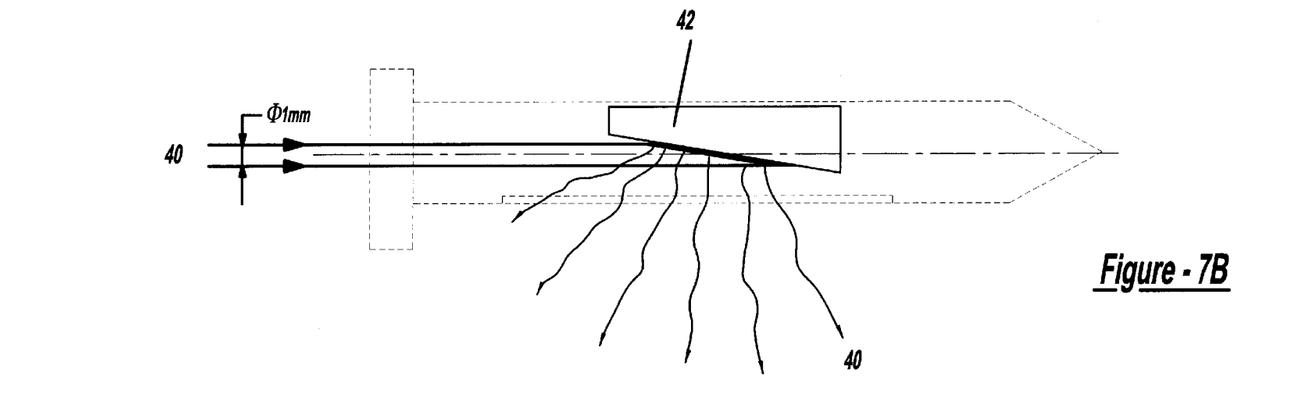

Instead of using a crystal 20 installed in the needle 17 (as it is shown on FIG. 4C) a bulk material (metal) can be used which plays the role of quasi-anode. In other words, metal 42 being irradiated emits characteristic x-rays. (FIGS. 6 and 7). For excitation of characteristic radiation, an incident x-ray beam 40 is used which has a higher energy than the potential of excitation of the quasi-anode characteristic line. For example, if a tungsten quasi-anode (the strongest characteristic line about 59 keV) is used in the needle 17, with energy above 69 keV (The potential applied to the x-ray source must be higher than 69 keV) is needed for the excitation x-ray.

The cross-section between incident beam and surface of the metal 42 can be considered as a new x-ray source, moreover, every point of this cross-section emits radiation in a hemispheric shape (FIGS. 6 and 7). Upon focusing conditioning optics with focus on the surface of the quasi-anode a point focus beam is produced. Using a parabolic conditioning optics and a relatively small angle between incident beam and the surface a linear focus beam can be produced with predetermined focus shape parameters. For example, for incident beam with 1 mm in diameter and angle of incidence 2° produces a linear focus beam of 29 mm×1 mm.

Figure 8A:
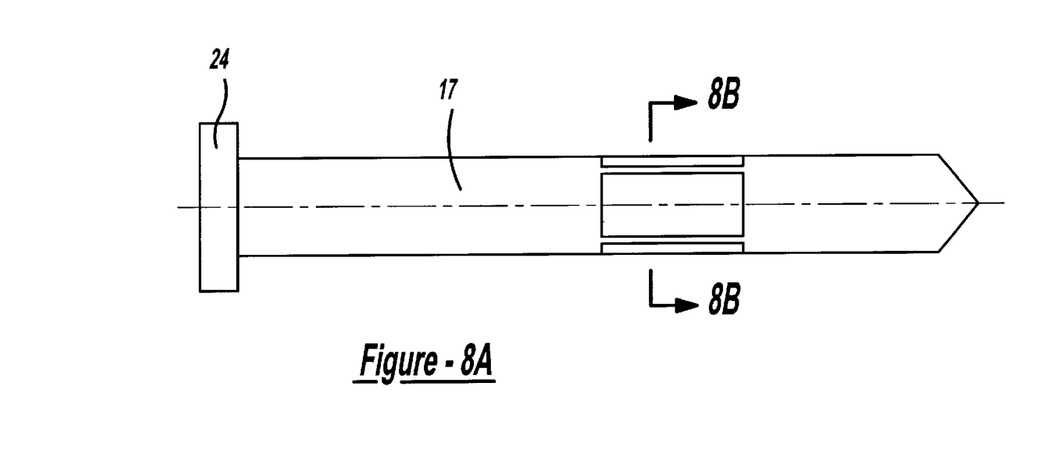
FIG. 8 is a schematic view and cross-sectional view of the needle with back windows which are used for transmitting of fluorescent x-rays emitting from a pyramidal quasi-anode.
Figure 8B:
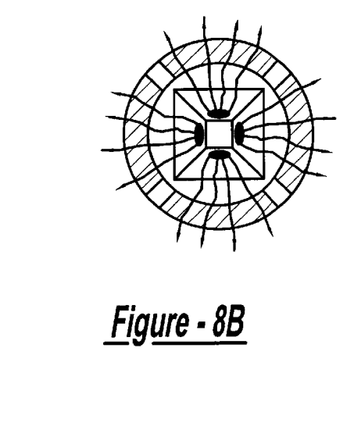
Figure 8C:
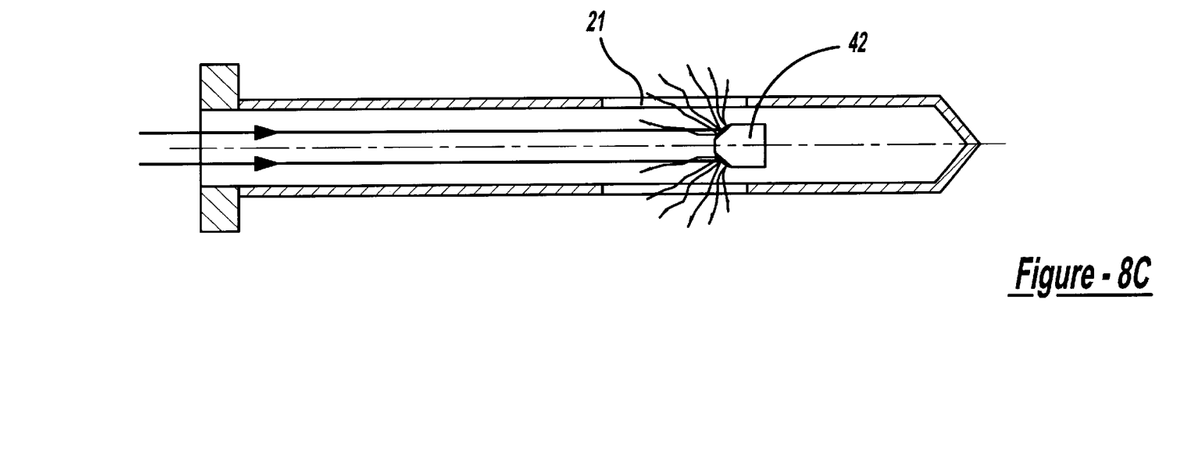

Using a metal quasi-anode 42 with a pyramid or cone shape as well as in the case of crystal 20 (FIG. 8), it is possible to use a different metal for every section of the pyramid producing different energy from different sides of the same quasi-anode.

It is also possible to use a metal coated end window of the needle 17 analogously known as the "transmitting" anode of conventional x-ray source. In this case a cross-section between parallel or focusing beam and the metal coated window can consider as a point or linear (in case of a few degree angle between an incident beam and the end window surface) x-ray source. The thickness of the coated metal depends on the energy of the incident x-ray beam 40 and z-number of the metal and can be found in literature describing x-ray sources with "transmitting" anodes. As in the case of a quasi-anode from bulk metal described above, in this case every point of focus emits radiation in hemisphere.

The x-ray system 10 (FIG. 1) x-ray source is a low energy (10 MeV), linear accelerator 46 (linac). The parabolic collimator/monochromator 50 (FIG. 2) creates a quasi-monochromatic (full width at half maximum—FWHM 10 kV) narrow (about 0.5 mm in cross-section) parallel x-ray beam 40 and directs it to the connector. The x-ray beam 40 is then directed to the hollow needle 17 (FIG. 6) which has a metallic quasi-anode. This quasi-anode can rotate and move inside of the needle 17 using special rods attached to the connector. The quasi-anode being irradiated can emit characteristic x-ray beams 40 with an energy defined by material of the quasi-anode.

The advantages of using linac as an x-ray source compared with an x-ray tube are as follows: 1. providing about two orders of magnitude higher efficiency (the ratio of output energy emitted as x-rays to the input energy deposited by electrons); and 2. the directed spatial distribution of the x-ray beam around a linac thin target.

Assuming that an x-ray source (linac) has the following parameters:

| | |
|---|---|
| P (average power) | 20 kW |
| U (x-ray beam) | 10 MV |
| Point focus | 0.3 mm (in diameter) |

It can be shown that:

$$Efficiency = 9 \times 10^{-10} ZV$$

It means that for tungsten target 42 (Z=74) and U=10 MV 66% of electron beam energy emitted as an x-ray radiation. However for low energy, efficiency can be significantly less due to necessity to use very thin (about 50 micron) anode to get favorable space distribution. For estimation 6% efficiency can be used.

Figure 9:
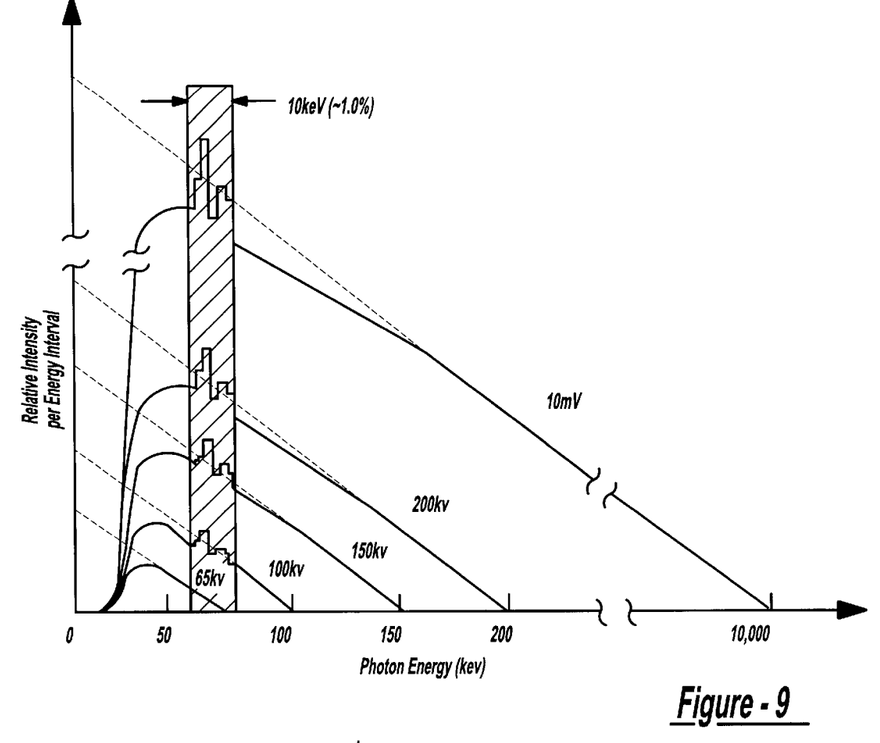
FIG. 9 is a graph showing the relative intensity per energy interval versus the photon energy of the x-ray beam.

It is known that for x-ray source characteristic lines represent more than 70% of the total intensity for Umax>$UK_{60}$. In other words, (FIG. 9) for an x-ray source with the Tungsten anode and, for example, Umax=100 kV intensity in the spectral region which includes $K_{60}$ and $K_{62}$ lines $_{67}$ U=10 kV as minimum seven times higher than δU/Umax. Using the same approach it can be determined that for a linac the spectral region from 60 kV to 70 kV (Tungsten anode) represent about 1% of the total output x-ray average energy.

A parabolic multilayer collimator built in accordance with the "side-by-side" Kirkpatrick-Baez scheme can be used with the following parameters:

Coefficient of reflectivity 20% (two reflection)

Full width of half maximum (FWHM) of multilayer optics 10 KV

Angular aperture of 0.3 degree (for energy from 60 kV to 70 kV).

Figure 10:
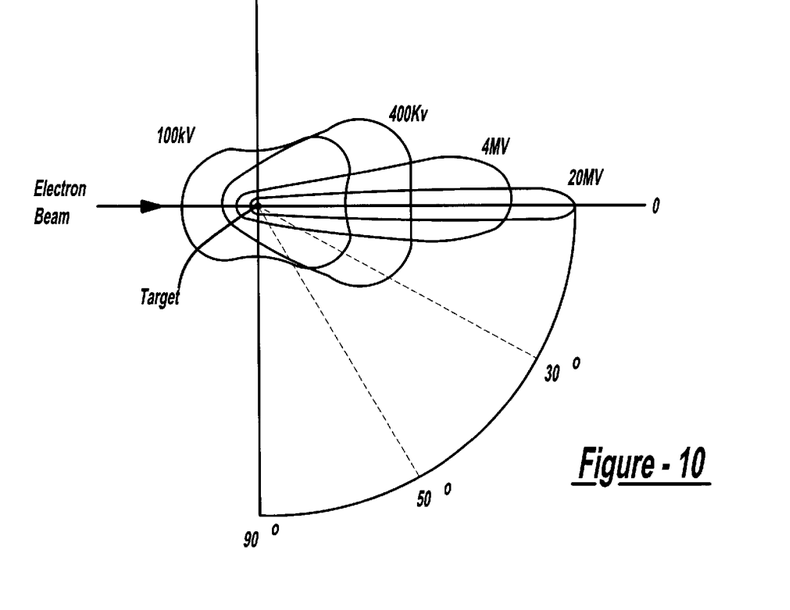
FIG. 10 is a schematic illustration of the spatial distribution of x-rays around a thin target.

Assuming (FIG. 10) that the spatial distribution of x-rays is defined as 5°×5°. An aperture of the parabolic collimator of 0.3°×0.3° can be used. The intensity of the flux for the central part of this distribution about 5 times higher than average.

The parabolic collimator/monochromator is able to transmit:

$$5*0.2*0.3 \times 0.3°)/(5° \times 5°) = 0.36\%$$

of the total average energy of emitting x-ray beams 40.

Finally, the power which is found on the exit of the collimator. Pcoll. (W)=0.06*20,000 (linac out put average power of x-ray beams)*0.01 (monochromatization)*× 0.0036 (transmission of collimator)=0.043 W Pcoll.=0.043 W Any decreasing of the x-ray beam 40 power can be neglected due to the absorption in air for an x-ray energy of 60 keV and a path of 1 m.

Needles 17 with Nd target 42 as a scattering x-ray source can also be used. The Nd potential of excitation is 43.6 KeV and the energy of the incident beam is from 60 to 70 keV. The efficiency of the "transformation" incident beam to fluorescent and scattering is more than 60%. This provides the power emitted to the hemisphere from the quasi-anode: Pemit.=0.5*0.6*0.043=0.013W=0.013 J/sec The time required to deliver dose of 500 rad (max allowed dose for one seance) to a 5 cm in diameter tumor (max size of a tumor) can therefore be calculated as follows:

| | |
|---|---|
| Volume of tumor | V = 65 cm^3 |
| Weight of tumor | P = 65 g |
| Irad = 0.01 J/kg: 500 rad = 5 j/kg = 0.3 J/tumor | |
| Time t = 0.3 (J/tumor)/.013 J/sec = 23 sec | |

Figure 11:
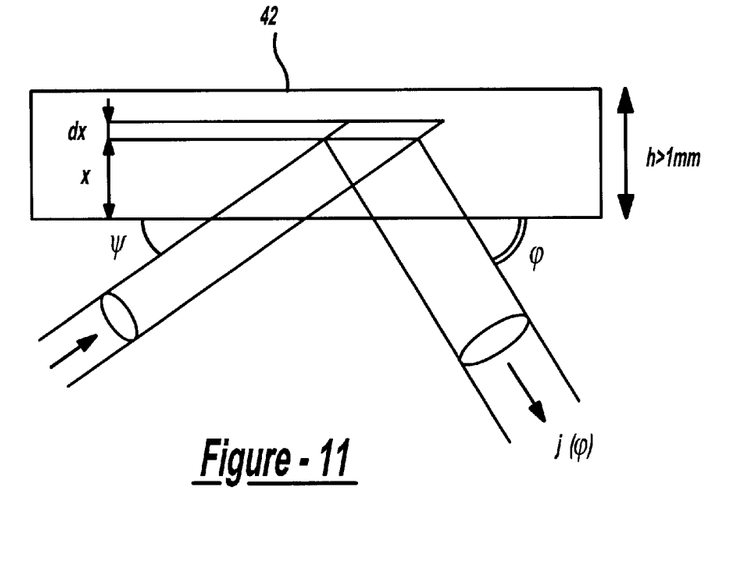
FIG. 11 is a schematic view of an alternative embodiment of the present invention.

First of all, provide the estimation of the spatial shape of the x-ray beam 40. The parallel primary beam incident on the metallic quasi-target 42 (FIG. 11) is at a constant angle Φ=10°. The beam is assumed to be monoenergetic (from 60 keV to 70 keV) with energy higher than energy of excitation (43.6 keV) Nd quasi-target 42. In this case a fluorescent, modified (Compton) and non-modified (Releight) scattering radiation is observed. The fluorescent radiation dominates (more than 95%), so for estimation only consider fluorescent radiation.

It is known that the fluorescent radiation is emitted uniformly in every direction. The self-attenuation of x-ray radiation plays the main role in the deformation of the semispherical beam shape. If angle φ (FIG. 11) changes from 0° to 180° the spatial distribution of the emitting beam intensity I(φ) follows the low;

$$I(\phi)=A/(1\sin\Theta+1/\sin\phi) \text{ where } A=\text{const.}$$

The walls of the needle 17 work as a filter for x-ray, absorbing the radiation and modifying spatial distribution. The spatial distribution for Mg—B alloy needle 17 (Nd quasi-target 42) is shown on (FIG. 6). For Mg—B needle 17, the integral loss of delivered energy is less than 15%; for Ti needle 17 less than 50%. By rotating the target 42 around the optical axis 16 the spatial distribution which is received is identical to spatial distribution 137Cs or 192Ir, the isotopes which most often are used in HDR Brachytherapy.

Figure 12:
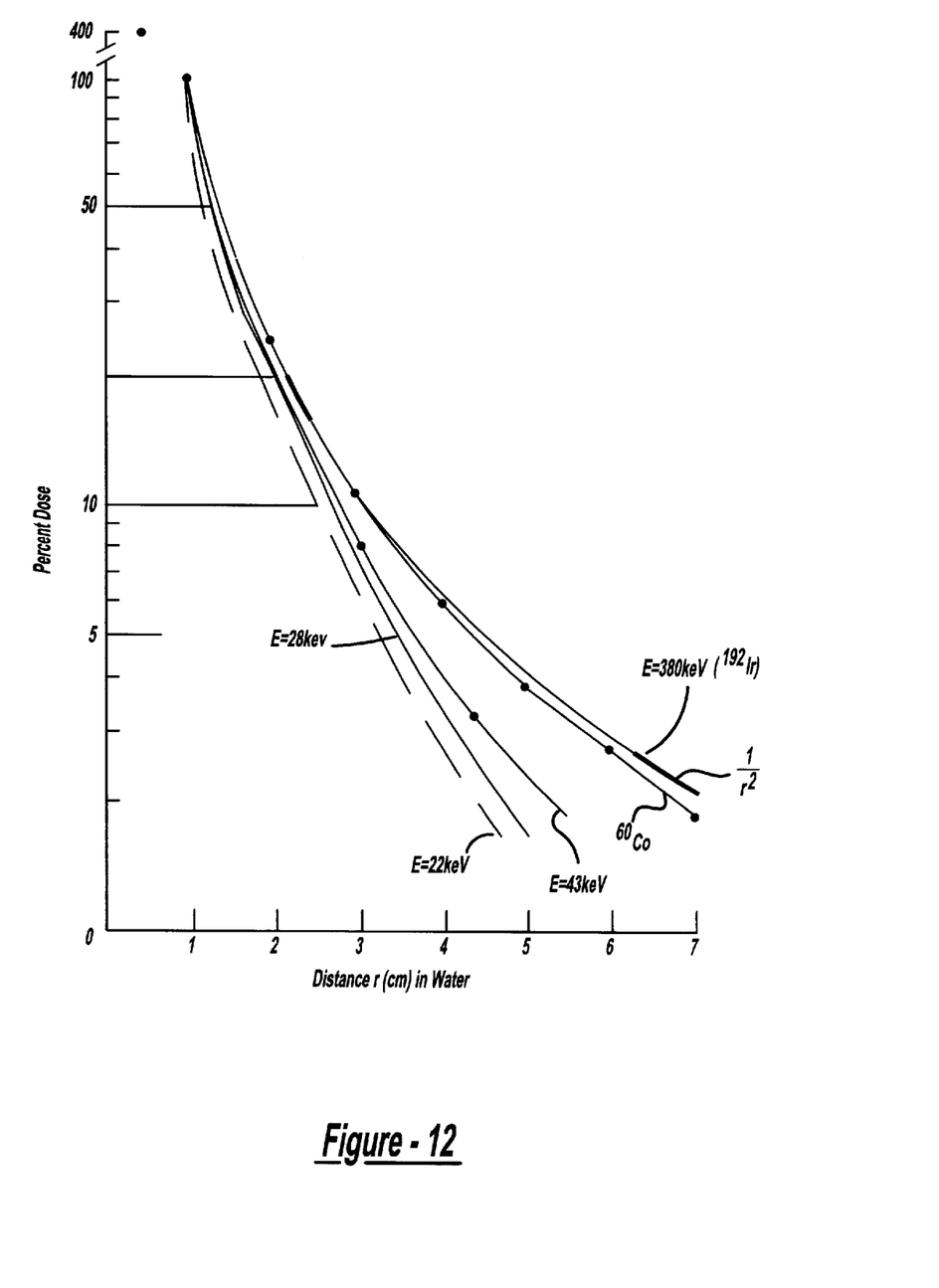
FIG. 12 is a graph showing the percent dose variation in water (analog of tissue) for radioactive isotopes and x-rays emitted from different metal quasi-anodes.

Isodose curves for $^{192}$Ir, $^{60}$Co and x-rays emitted from different metal targets are shown on the (FIG. 12). It is easy to see that the considered method is significantly more flexible for delivering isodose in tumors of different shapes. The main reason being the ability to modify the spatial shape of the emitted radiation and the ability to change the "fall off" curves for dose variation.

Figure 13A:
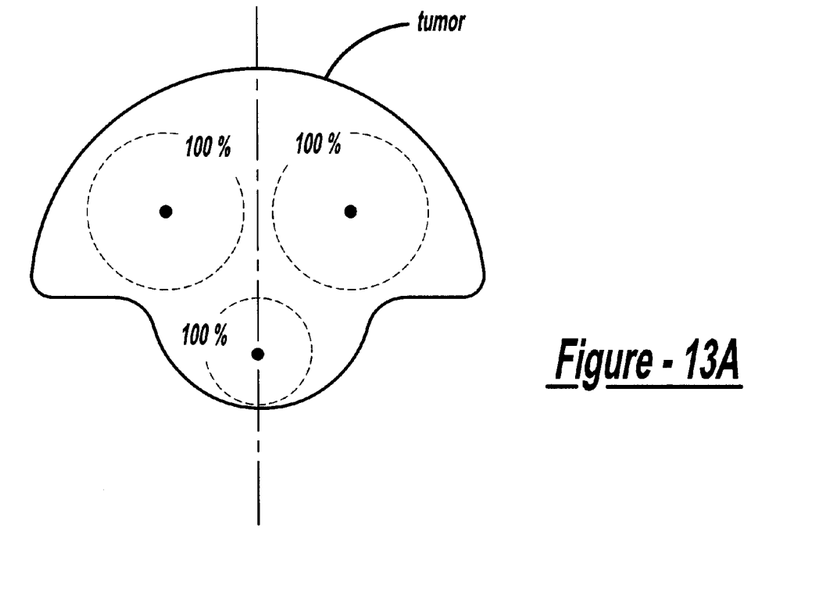
Figure 13B:
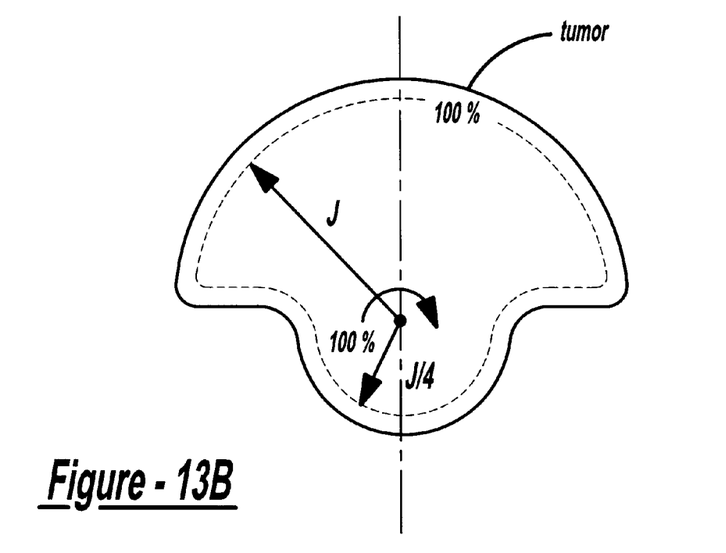

To illustrate the difference in the flexibility between two methods consider the tumor with cross section (FIG. 13). Due to isotopes having uniform space distribution, it is rather obvious that it is necessary to use as minimum three needles 17 to deliver 100% dose (HRD Brachytherapy) and only one needle 17 in the considered case.

The invention may be embodied in other specific forms without departing from the spirit or essential characteristics thereof. The present embodiments are therefore to be considered in all respects as illustrative and not restrictive.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. The x-ray system or parts of the x-ray system for example, the linac with the coupled conditioning optics, can be used as an extremely intensive x-ray source (more than 2 order of magnitude higher than x-ray tube coupled with the same conditioning optics) in analytical instrumentation, semiconductor industry (surface analysis etc.), nondestructive analysis, etc. It is, therefore, to be understood that within the scope of the described invention, the invention may be practiced otherwise than as specifically described.

REFERENCES

1. U.S. Pat. No. 5,153,900 to Nomikos.
2. U.S. Pat. No. 5,369,679 to Sliski.
3. U.S. Pat. No. 5,428,658 to Oetittinger.
4. U.S. Pat. No. 5,422,926 to Smith.
5. U.S. Pat. No. 5,528,652 to Smith.
6. U.S. Pat. No. 5,566,221 to Smith.
7. U.S. Pat. No. 5,646,976 to Gutman.
8. U.S. Pat. No. 5,799,056 to Gutman.

What is claimed is:

1. An x-ray system for treating cancer by delivering an x-ray beam with a predefined energy, intensity and spatial distribution directly to a desired region of tissue, including tumors, comprising:

an x-ray source for creating x-ray radiation;

conditioning optics which collimate or focus and direct the x-ray radiation;

an expanding pipe guide in optical communication with the conditioning optics; and an implantable needle in optical communication with the expanding pipe guide, the needle having an optical axis and including means for shaping the x-ray beam delivered to the tissue, the means for shaping being installed across the optical axis of the needle.

2. The x-ray system according to claim 1, wherein said x-ray source is a linear accelerator.

3. The x-ray system according to claim 2, wherein the linear accelerator has an anode with a thickness that does not exceed 50 microns.

4. The x-ray system according to claim 2, wherein the implantable needle has transparent walls.

5. The x-ray system according to claim 4, wherein the means for shaping includes a secondary target that serves as a quasi-anode for absorbing an incident x-ray beam and emitting x-rays, the quasi-anode means being installed across the incident x-ray beam.

6. The x-ray system according to claim 5, wherein the quasi-anode means is made of a bulk material.

7. The x-ray system according to claim 2, including slits in the linear accelerator through which the x-ray beam passes, the slits being located between the x-ray source and the implantable needle.

8. The x-ray system according to claim 2, wherein the expanding pipe guide includes rotational means for rotating the implantable needle around the x-ray beam.

9. The x-ray system according to claim 1, wherein the implantable needle includes one or more side windows.

10. The x-ray system according to 9, wherein the implantable needle includes a reflecting crystal installed across the x-ray beam in proximity to the one or more side windows.

11. The x-ray system according to claim 10, wherein the reflecting crystal has a shape selected from the group consisting of a pyramid, a cone, and a flat disc.

12. The x-ray system according to claim 10, wherein the reflecting crystal has a defined cut-off angle (ψ).

13. The x-ray system according to claim 1, wherein the conditioning optics include means for creating a point focus beam which focuses on the surface of the means for shaping.

14. The x-ray system according to claim 1, further including collimating conditioning optics that include means for creating a parallel x-ray beam.

15. A method of treating tumors, including cancers, comprising the steps of:

generating a directed x-ray beam having a predetermined energy and intensity;

directing the x-ray beam through an implantable needle including means for shaping the x-ray beam to create a shaped x-ray beam;

irradiating a desired part of a tumor with the shaped x-ray beam in accordance with predefined treatment requirements.

* * * * *